United States Patent [19]

Sykes et al.

[11] Patent Number: 4,503,218
[45] Date of Patent: Mar. 5, 1985

[54] ANTIBIOTIC CEPACIN

[75] Inventors: Richard B. Sykes, Belle Mead; William L. Parker, Pennington, both of N.J.

[73] Assignee: E. R. Squibb & Sons, Inc., Princeton, N.J.

[21] Appl. No.: 495,010

[22] Filed: May 16, 1983

[51] Int. Cl.$^3$ .................. C07D 407/14; C07D 407/06
[52] U.S. Cl. ................................................. 549/320
[58] Field of Search ......................... 549/320; 542/441

[56] References Cited

PUBLICATIONS

Journal of the Chemical Society, 2048–2055, (1963).
Journal of the Chemical Society, 4270–6, (1955).
Journal of the American Chemical Society, vol. 75, 1372–6, (1953).

Primary Examiner—Norma S. Milestone
Attorney, Agent, or Firm—Levinson, Lawrence S.; Donald J. Barrack

[57] ABSTRACT

Cultivation of a strain of the microorganism *Pseudomonas cepacia* SC 11,783, A.T.C.C. No. 39356 yields a novel antibiotic substance which is made up of two compounds, i.e., 5-[3-[3-(hepta-1,2-dien-4,6-diynyl)oxiran-2-yl]-3-hydroxy-1-propanyl]dihydro-2(3H)-furanone and 5-[[3-[3-(hepta-1,2-dien-4,6-diynyl)-2-oxiranyl]-2-oxiranyl]hydroxymethyl]dihydro-2(3H)-furanone.

2 Claims, No Drawings

ANTIBIOTIC CEPACIN

SUMMARY OF THE INVENTION

Cultivation of a strain of the microorganism *Pseudomonas cepacia* SC11,783, which has been deposited in the American Type Culture Collection as A.T.C.C. No. 39356, yields a novel antibiotic substance cepacin.

Cepacin has been analyzed and found to be made up of two compounds; i.e., 5-[3-[3-(hepta-1,2-dien-4,6-diynyl)oxiran-2-yl]-3-hydroxy-1-propenyl]dihydro-2(3H)-furanone, a compound of the formula

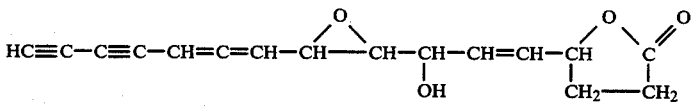

referred to as cepacin A, and 5-[[3-[3-(hepta-1,2-dien-4,6-diynyl)-2-oxiranyl]-2-oxiranyl]hydroxymethyl]-dihydro-2(3H)-furanone, a compound having the formula

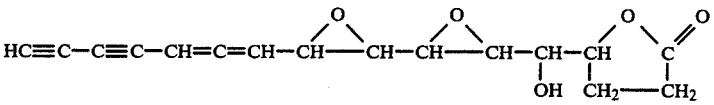

referred to as cepacin B.

Each of the above compounds exhibits activity against gram-positive bacteria. Cepacin A shows activity against some gram-negative bacteria and cepacin B shows activity against a wider range of gram-negative bacteria.

DETAILED DESCRIPTION OF THE INVENTION

The Microorganism

The microorganism used for the production of cepacin is *Pseudomonas cepacia*, SC 11,783. A subculture of the microorganism can be obtained from the permanent collection of the American Type Culture Collection, Rockville, Md. Its accession number in the repository is A.T.C.C. No. 39356. In addition to the specific microorganism described and characterized herein, it should be understood that mutants of the microorganism (e.g., mutants produced through the use of x-rays, ultraviolet radiation or nitrogen mustards) can also be cultivated to produce cepacin.

Isolation of *Pseudomonas cepacia* SC 11,783 from a soil sample (obtained in West Windsor, N.J.) in which it is present can be accomplished by plating the soil onto an agar of the following composition:

[1]Synthetic Sea Salts—1.0 grams
Aspartic Acid—0.05 grams
Asparagine—0.05 grams
Yeast Extract—1.0 grams
$KH_2PO_4$—0.02 grams
$K_2HPO_4$—0.02 grams
[2]Compost Extract—300.0 ml
Distilled Water—700.0 ml
Glycerol—5.0 ml The medium is adjusted to pH about 6.5 and sterilized in an autoclave at 121° C. for 30 minutes. After cooling to room temperature, the sterile and cooled medium is supplemented with the following:

[3]Biotin (0.1% solution)—1.0 ml
[3]Thiamin (0.2% solution)—1.0 ml
[3]Actidione (1.0% solution)—10.0 ml

[1] Synthetic Sea Salts—commercially available as Instant Ocean from Sea Aquarium Systems, 33208 Lakeland Blvd., Eastlake, Ohio 44094.
[2] Compost Extract—prepared by bringing to a boil a suspension of leaf litter in tap water (2:1, v/v) and then allowing to simmer for about 30 minutes. After cooling, the extract is filtered initially through cheesecloth and finally through Whatman 4 filter paper. The resulting liquid is sterilized by autoclaving at 121° C. for 20 minutes.
[3] These solutions are filter-sterilized.

After 24–72 hours incubation at 28° C., the colonies of *Pseudomanas cepacia* SC 11,783 are isolated from the plated soil. The isolated colonies are picked off and maintained on an agar medium composed of:

Yeast Extract—1 gram
Beef Extract—1 gram
NZ Amine A—2 grams
Glucose—10 grams
Agar—15 grams
Distilled Water to —1000 ml The medium is adjusted to pH 7.3 and sterilized in an autoclave at 121° C. for 30 minutes.

*Pseudomonas cepacia* SC 11,783 is a gram negative rod, motile by means of multitrichous polar flagella. It is non-fluorescent, oxidase positive, accumulates poly β-hydroxybutyrate as intracellular reserve material. Arginine dihydrolase is lacking, nitrate is reduced to nitrate, and growth occurs at 41° C.

The following compounds are utilized as the sole carbon source on the basal medium described in Stanier et al., *J. Gen. Microbiol*, 43:159 (1966): glucose, xylose, arabinose, fructose, sucrose, ribose, mannitol, sorbitol, salicin, acetate, citrate, d-tartrate, and putrescine. Rhamnose, maltose, lactose, erythritol are not utilized.

*Pseudomonas cepacia* SC 11,783 is identical to *Pseudomonas cepacia* A.T.C.C. No. 17759 and matches the published description of this species (Ballard et al., *J. Gen. Microbiol*, 60:199 (1970)) except for the failure to produce a yellow intracellular pigment.

Production of the Antibiotic

*Pseudomonas cepacia* SC 11,783 produces cepacin. To form cepacin according to the preferred methodology, the microorganism is grown at, or near, room temperature (25° C.) under submerged aerobic conditions in an aqueous nutrient medium containing an assimilable carbohydrate and nitrogen source. The fermentation is carried out until substantially activity is imparted to the medium, usually about 12 to 40 hours, preferably about 18 to 20 hours.

At harvest, cells can be removed by centrifugation. Cepacin can be extracted from the supernate into moderately polar organic solvents (e.g., n-butanol, ethyl acetate, chloroform, and dichloromethane) and can then be purified by normal-phase chromatography on silica gel or silicic acid or by partition chromatography on Sephadex LH-20 in methanol-chloroform-heptane (1:3:6) to give cepacin A and cepacin B in approximately equal amounts. These antibiotics can also be separated by reverse-phase chromatography on a Waters $C_{18}$ μBondapak column eluting with acetonitrile-water (3:7), and monitoring the effluent at 261 nm.

Cepacin A and cepacin B are very unstable when all the solvent is removed and decompose rapidly to give a dark brown insoluble solid. They should, therefore, be stored in dilute solution. They are also very base labile, rearranging to a triyne-ene system. This rearrangement has been observed in ethanol-water (1:9) without added base, presumably catalyzed by traces of base on the glassware. The γ-lactone ring is subject to methanolysis so storage in methanol should be avoided.

The following examples further illustrate the preparation and isolation of cepacin A and cepacin B.

EXAMPLE OF FERMENTATION OF PSEUDOMONAS CEPACIA SC 11,783

*Pseudomonas cepacia* SC 11,783 was maintained on the following sterilized agar medium (A):

|  | Grams |
| --- | --- |
| Yeast Extract | 1.0 |
| Beef Extract | 1.0 |
| NZ Amine A | 2.0 |
| Glucose | 10.0 |
| Agar | 15.0 |
| Distilled H$_2$O to 1 liter | |

The pH was adjusted to 7.3 before sterilization at 121° C. for 30 minutes. A loopful of surface growth from an agar slant (Medium A) of *Pseudomonas cepacia* SC 11,783 was used to inoculate each of four 500 ml Erlenmeyer flasks containing 100 ml each of the following sterilized medium (B):

|  | Grams |
| --- | --- |
| Yeast Extract | 4.0 |
| Malt Extract | 10.0 |
| Dextrose | 4.0 |
| Distilled H$_2$O to 1 liter | |

The pH was adjusted to 7.3 before sterilization at 121° C. for 15 minutes. After inoculation, the flasks were then incubated at 25° C. on a rotary shaker (300 rpm; 2 inch stroke) for approximately 24 hours. After incubation as described above, 1% (vol/vol) transfers were made from the grown culture flasks to thirty 500 ml Erlenmeyer flasks each containing 100 ml of sterilized medium (B), as described above. After inoculation, the flasks were once again incubated at 25° C. on a rotary shaker (300 rpm; 2 inch stroke) for approximately 24 hours. After incubation as described above, a 1% transfer (vol/vol) was made to a 380-liter stainless steel fermentation tank containing 250 liters of sterilized medium (B). After inoculation the fermentation was continued under the following conditions: temperature 25° C.; pressure 10 psig; aeration—10 CFM; agitation 155 rpm. Ucon LB-625 (polypropylene glycol; Union Carbide) was added as needed as an antifoam agent. After approximately 18-20 hours, the fermentation was completed. The fermentation broth was then adjusted to pH 5.0 using hydrochloric acid and the broth contents of the tank was centrifuged yielding approximately 240 liters of supernatant broth.

EXAMPLE OF ISOLATION OF CEPACIN FROM A 50 LITER FERMENTATION

The broth supernate (pH 6) from a 50 liter fermentation of *Pseudomonas cepacia* SC 11,783 was extracted with 16 liters of dichloromethane and the extract was concentrated in vacuo to 700 ml. The concentrate was dried (sodium sulfate), taken to dryness, and the residue immediately redissolved in chloroform-heptane-methanol-water (2:3:4:1) (system I). The lower (water rich) phase was separated, washed once with an equal volume of the upper phase of system I, and then concentrated to 50 ml in vacuo. The concentrate was extracted with 25 ml of chloroform, giving 45 ml of lower phase, LP-1, that was stored in the freezer until further purification[1]. The solution contained 180 mg of non-volatile material, ca. 50 mg. of which was cepacin A and cepacin B judging from the UV absorbance at 263 nm.

[1]The solution should have been concentrated to remove all methanol and then diluted with chloroform before storage.

LP-1 was concentrated in vacuo and the residue immediately dissolved in 5 ml of methanolchloroform-heptane (1:3:6) (system II). The solution was chromatographed on a 2.5×90-cm (450 ml) column of Sephadex LH-20 in system II, eluting at 2 ml/minute and collecting 20 ml fractions. Cepacin A and cepacin B were located by UV absorbance at 263 nm. Fractions 95 to 103 were combined, concentrated in vacuo to 5 ml and diluted with chloroform to give 35 ml of solution which contained 6.8 mg of cepacin A: UV max in CHCl$_3$(E$^{1\%}$) 248.5 (613), 262.0 (827), 276.8 nm (672); nmr in CDCl$_3$+CD$_3$OD δ2.05 (1H, m), 2.47 (1H, m), 2.50 (1H, m. J<1 Hz), 2.58 (1H, m), 3.02 (1H, J=4.6, 2.1 Hz, Δδ=0.01 ppm), 3.47 (1H, J=7.8, 2.0, 0.6 Hz), 4.17 (1H, m), 5.03 (1H, m), 5.33 (1H, J=7.9, 6.8, 0.6 Hz), 5.68 (1H, J=6.7 Hz), 5.91 ppm, (2H, m); ir in CHCl$_3$ 3291, 2218, 1944, 1770, 1177 cm$^{-1}$; [α]$_D$ (c=0.23 in CHCl$_3$) −129°.

Similarly, fractions 108 to 119 gave 35 ml of solution which contained 10.7 mg of cepacin B: UV max in CHCl$_3$(E$^{1\%}$) 250.5 (399), 263.7 (575), 279.0 (465); nmr in CDCl$_3$+CD$_3$OD δ2.31 (1H, m), 2.52 (1H, m, J<1 Hz), 2.55 (1H, J=17.9, 9.6, 8.2 Hz), 2.66 (1H, J=17.9, 9.8, 5.7 Hz), 3.01 (1H, J=4.3, 1.8 Hz), 3.15 (1H, J=4.3, 2.1 Hz), 3.21 (1H, J=4.0, 2.1 Hz), 3.46 (1H, J=7.9, 1.9, 0.6 Hz), 3.69 (1H, J=4.0, 4.0 Hz), 4.61 (1H, J=7.0, 7.0, 3.6 Hz), 5.31 (1H, J=7.9, 6.7, 0.6 Hz), 5.70 ppm (1H, J=6.7, 0.9, 0.9 Hz); ir in CHCl$_3$ 3295, 2217, 2197, 1946, 1773, 1180 cm$^{-1}$.

EXAMPLE OF ISOLATION OF CEPACIN A FROM A 250 LITER FERMENTATION

Cepacin was extracted with dichloromethane from 200 liters of broth supernate, partitioned in chloroform-heptane-methanol-water (2:3:4:1), and extracted into chloroform as described in the previous example. The chloroform extract was applied to a 1 liter column of Whatman LPS-1 silica gel. The column was washed with 1 liter of chloroform and then eluted with chloroform-ethyl acetate (3:1), collecting 250 ml fractions. The effluent was monitored by TLC on silica gel (chloroform-ethyl acetate (1:1), detection, with phosphomolybdic acid; cepacin A, R$_f$ 0.19; cepacin B, R$_f$ 0.13). Fractions 6 and 7 contained cepacin A and fractions 9 to 12 contained cepacin B. Both of the compounds were about 50% pure at this stage and were further purified by partition chromatography on Sephadex LH-20 in methanol-chloroform-heptane (1:3:6) as described in the previous example.

Biological Activity

The following methodology is used to determine the minimum inhibitory concentration (hereinafter referred to as MIC) of the compounds of this invention.

The test organisms are grown in approximately 15-20 ml of Antibiotic Assay broth (Difco) by inoculating (in tubes) the broth with a loopful of the organism from a BHI (Difco) agar slant. The inoculated tubes are incubated at 37° C. for 18 to 20 hours. These cultures are assumed to contain $10^9$ colony forming units (hereinafter CFU) per milliliter. The cultures are diluted 1:100 to give a final inoculum level of $10^7$ CFU; dilutions were made with K-10 broth*.

The compounds are dissolved in the appropriate diluent at a concentration of 1000 µg/ml. Two-fold dilutions are made in K-10 broth resulting in a range from 1000 µg/ml to 0.5 µg/ml. 1.5 ml of each dilution is placed into individual square petri dishes to which 13.5 ml of K-10 agar** is added. The final drug concentration in the agar ranges from 100 µg/ml to 0.05 µg/ml. Organism growth control plates containing agar only are prepared and inoculated before and after the test plates. The organisms are applied to the agar surface of each plate with the Denley Multipoint Inoculator (which delivers approximately 0.001 ml of each organism) resulting in a final innoculum level of $10^4$ CFU on the agar surface.

*K-10 broth is a yeast beef broth containing:
Beef extract—1.5 g
Yeast extract—3.0 g
Peptone—6.0 g
Dextrose—1.0 g
Distilled water q.s. 1 liter

**K-10 agar
Beef extract—1.5 g
Yeast extract—3.0 g
Peptone—6.0 g
Dextrose—1.0 g
Agar—15.0 g
Distilled water q.s. 1 liter The plates are incubated at 37° C. for 18 hours and the MIC's are determined. The MIC is the lowest concentration of compound inhibiting growth of the organism.

The tables that follow are tabulated results obtained when the compounds of this invention were tested against various organisms. The number following each organism refers to the number of the organism in the collection of E. R. Squibb & Sons, Inc., Princeton, N.J. A dash (-) in the tables means that the compound tested did not show activity against the particular organism at 50 µg/ml.

| Organism | SC#* | M.I.C. (µg/ml) Cepacin A | Cepacin B |
|---|---|---|---|
| Staphylococcus aureus | 1276 | 0.2 | <0.05 |
| Staphylococcus aureus | 2399 | 0.1 | <0.05 |
| Staphylococcus aureus | 2400 | 0.2 | <0.05 |
| Staphylococcus aureus | 10165 | 0.2 | <0.05 |
| Streptococcus faecalis | 9011 | 50 | — |
| Streptococcus agalactiae | 9287 | 50 | — |
| Micrococcus luteus | 2495 | 0.2 | 3.13 |
| Escherichia coli | 8294 | 50 | 0.78 |
| Escherichia coli | 10857 | 1.6 | 0.1 |
| Escherichia coli | 10896 | 12.5 | 0.4 |
| Escherichia coli | 10909 | 6.3 | 0.2 |
| Klebsiella aerogenes | 10440 | — | 0.78 |
| Klebsiella pneumoniae | 9527 | — | — |
| Proteus mirabilis | 3855 | — | 6.3 |
| Proteus rettgeri | 8479 | >25 | 6.3 |
| Proteus vulgaris | 9416 | 1.6 | <0.05 |
| Salmonella typhosa | 1195 | 25 | 0.4 |
| Shigella sonnei | 8449 | 50 | 0.8 |
| Enterobacter aleacae | 8236 | — | 25 |
| Enterobacter aerogenes | 10078 | — | 3.1 |
| Citrobacter freundii | 9518 | 50 | 0.8 |
| Serratia marcescens | 9783 | — | — |
| Pseudomonas aeruginosa | 9545 | — | — |
| Pseudomonas aeruginosa | 8329 | — | — |
| Acinetobacter calcoacetieus | 8333 | — | — |

*Organisms from the culture collection of E. R. Squibb & Sons, Inc.

What is claimed is:
1. 5-[3-[3-(hepta-1,2-dien-4,6-diynyl)oxiran-2-yl[-3-hydroxy-1-propenyl]dihydro-2(3H)-furanone.
2. 5-[[3-[3-(hepta-1,2-dien-4,6-diynyl)-2-oxiranyl]-2-oxiranyl]hydroxymethyl]dihydro-2(3H)-furanone.

* * * * *